United States Patent
Groves et al.

(10) Patent No.: US 7,903,782 B2
(45) Date of Patent: Mar. 8, 2011

(54) APPARATUS AND METHOD FOR FLUID PHASE FRACTION DETERMINATION USING X-RAYS OPTIMIZED FOR WET GAS

(75) Inventors: Joel L. Groves, Leonia, NJ (US);
Etienne Vallee, Princeton, NJ (US);
Peter Wraight, Skillman, NJ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/959,917

(22) Filed: Dec. 19, 2007

(65) Prior Publication Data
US 2009/0161823 A1 Jun. 25, 2009

(51) Int. Cl.
*G01N 23/06* (2006.01)
(52) U.S. Cl. ........... 378/53; 378/156; 250/256; 250/264; 250/265
(58) Field of Classification Search ................. 378/53, 378/156; 250/256, 264, 265
See application file for complete search history.

(56) References Cited

U.S. PATENT DOCUMENTS

| | | | |
|---|---|---|---|
| 4,499,591 A * | 2/1985 | Hartwell | 378/62 |
| 4,879,463 A | 11/1989 | Wraight et al. | |
| 5,689,540 A | 11/1997 | Stephenson et al. | |
| 6,097,786 A | 8/2000 | Groves et al. | |
| 6,246,747 B1 * | 6/2001 | Wear et al. | 378/98.9 |
| 6,335,959 B1 * | 1/2002 | Lynch et al. | 378/45 |
| 2004/0240606 A1 * | 12/2004 | Laurila et al. | 378/45 |
| 2005/0163284 A1 * | 7/2005 | Inazuru | 378/108 |
| 2007/0114372 A1 * | 5/2007 | Lievois et al. | 250/269.1 |

FOREIGN PATENT DOCUMENTS
WO WO0196902 12/2001

\* cited by examiner

*Primary Examiner* — Hoon Song
*Assistant Examiner* — Mona M Sanei

(57) ABSTRACT

An apparatus for determining fractional amounts of each phase of a multiple phase fluid includes an x-ray generator includes a sample chamber is configured to admit therein a sample of fluid for analysis. The chamber is disposed in a radiation path output from the generator. A filter is disposed in the radiation path between the output of the generator and the radiation input of the sample chamber. A first radiation detector is positioned in a radiation path from the sample chamber after radiation has passed through the sample chamber. A thickness and a material of the filter are selected to optimize resolution of radiation detected by the first detector to changes in volume fraction of oil and water in the fluid sample when a gas fraction thereof is between about 90 to 100 percent.

14 Claims, 6 Drawing Sheets

APPARATUS AND METHOD FOR FLUID PHASE FRACTION DETERMINATION USING X-RAYS OPTIMIZED FOR WET GAS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention relates generally to the field of measurement of fluid properties using x-ray radiation. More particularly, the invention relates to x-ray radiation methods and apparatus for determining fluid phase fractions of multiple phase fluids wherein gas comprises a majority of the fluid under examination.

2. Background Art

Wellbores are drilled through subsurface Earth formations for the purpose of extracting useful fluids from the subsurface formations, such as petroleum. Typically, when formation fluid is extracted from the formations and is moved into a wellbore, it consists of a mixture of various fractions of oil, gas, and water. Certain well operations, for example, include pumping fluid such as water, natural gas or carbon dioxide into a wellbore drilled through the same formations and adjacent to a fluid-producing wellbore to help force formation fluid from the formations into the fluid-producing wellbore. A phase fraction meter is useful in such instances to dispose in the fluid-producing wellbore to show when unwanted fluids, such as water, carbon dioxide or natural gas are being extracted from a particular subsurface formation along with the desired fluid, such as oil. Information concerning the fractional volume of particular fluids being extracted from a wellbore is also useful in optimizing the production of fluid from a subsurface reservoir. The gas to liquid ratio, and the oil to water ratio, for example, are important and constant monitoring of such ratios can assist in determining the best utilization of a reservoir.

Additionally, fluid that is high fractional volume of water will be of less monetary worth than fluid having a high fractional volume other components, such as gas and oil. By determining the fractional volumes of each of gas, oil and water early in the process of extracting fluid from a reservoir, it is possible to estimate the economic value of any given operation affecting fluid production from a subsurface reservoir. By testing fluid when delivered from an unknown source, it is also possible for a buyer of produced fluids to determine if the fluid fractions represented by the fluid producer are what are in fact being provided by the fluid producer.

One approach for determining fluid fractional composition known in the art includes a separator or a large tank used to physically store some amount of fluid extracted from a well. Segregating the various fluid components is performed in the tank through a gravity-based process. Such process requires stable conditions inside the separator, and the results may take an extended period of time to obtain. The required degree of condition stability may be difficult or even impossible to obtain, and because of the extended time needed to obtain fluid component separation such technique may create an obstacle to economic recovery of hydrocarbons because flow from the wellbore must be stopped during the testing process. Separator-based systems can also provide erroneous results when there is some commingling of the various fluid components ("phases"). Additionally, viscous fluids such as heavy oil make accurate separation and testing difficult.

Other systems known in the art may allow for substantially "real-time" phase fraction determination using a radiation source and detector. Such fractional composition measuring devices use chemical isotope radiation sources and may be deployed for long periods of time in unattended locations. The locations often are not secure and may encounter variable ambient environmental conditions. Security and environmental risks associated with chemical isotope radiation sources makes it desirable to use non-chemical radiation sources for fluid fractional composition measuring devices. Electrical radiation generators would alleviate some of the foregoing concerns, but most electrical radiation generators (such as x-ray generators) have radiation output that is related to the degree of accuracy with which actuation voltage and target current can be controlled. As a result there are certain benefits to the use of chemical sources. Specifically, the change of their output radiation over time is stable, enabling such sources to provide a highly predictable radiation flux.

An example of using an electrically powered x-ray generator for fractional fluid volume composition determination is described in U.S. Pat. No. 5,689,540 issued to Stephenson et al. and assigned to the assignee of the present invention. The device described in the Stephenson et al. '540 patent is a system for imparting a spectrum of photon radiation through a fluid sample and determining a fluid fraction by analysis of detected radiation after it has passed through the fluid sample.

Another device is described in U.S. patent application Ser. No. 11/425,285 filed on Jun. 20, 2006, entitled, "HIGH PERFORMANCE X-RAY MULTIPHASE FRACTION METER" and assigned to the assignee of the present invention. Such device includes an x-ray generator with a special filter disposed in the output of the x-ray generator. Filtered x-rays from the generator are detected both at a reference detector, which is essentially disposed directly in the radiation output of the generator, and a measurement detector, which is disposed along a radiation path through a chamber in which a sample of the fluid under analysis is disposed. Fractional volumes of three different phases, gas, oil and water may be determined by analysis of the radiation detected by the measurement detector. Measurements from the reference detector are used to automatically control various operating parameters of the x-ray generator so that analysis of the measurement detector signal is relatively unaffected by changes in x-ray generator output. The system disclosed in the foregoing patent application is susceptible to improvement in accuracy under conditions that include high fractional volume of gas, e.g., 90 percent or more gas volume fraction, in the fluid being examined. Accordingly, it is desirable to have a multiple phase fluid fraction analysis device that has improved accuracy under conditions of high fractional volume of gas.

SUMMARY OF THE INVENTION

An apparatus for determining fractional amounts of each phase of a multiple phase fluid includes an x-ray generator. A sample chamber is configured to admit therein a sample of fluid for analysis. The chamber is disposed in a radiation path output from the generator. A filter is disposed in the radiation path between the output of the generator and the radiation input of the sample chamber. A first radiation detector is positioned in a radiation path from the sample chamber after radiation has passed through the sample chamber. A thickness and a material of the filter are selected to optimize resolution of radiation detected by the first detector to changes in volume fraction of oil and water in the fluid sample when a gas fraction thereof is between about 90 to 100 percent.

A method for determining volume fraction of selected components of a fluid according to another aspect of the invention includes generating x-rays by accelerating electrons into a target material. The acceleration of electrons is controlled and the generated x-rays are filtered such that the filtered x-rays have a predetermined energy spectrum optimized to resolve volume fractions of oil and water disposed in gas, wherein a volume fraction of the gas is between about 90 and 100 percent. The filtered x-rays are passed through a sample of the fluid. X-rays within selected energy ranges that have passed through the fluid sample are detected. Fractional volumes of gas, oil and water are determined from the detected x-rays.

Other aspects and advantages of the invention will be apparent from the following description and the appended claims.

DETAILED DESCRIPTION

A device according to various aspects of the invention may be used within a wellbore drilled through subsurface Earth formations. The device according to the invention may also be used to monitor oil/gas well effluents, and may be situated on the Earth's surface, either at the bottom of the sea on a submersible structure, or on an offshore platform, or on land. When used in wellbores, such device may be conveyed by armored electrical cable ("wireline"), in a "string" of drill pipe or tubing, by coiled tubing, by slickline, or by any other conveyance mechanism known in the art. A device according to the invention may also be permanently emplaced in a wellbore. Accordingly, the device is described without regard to its manner of disposition, its place of disposition or any means of conveyance as the foregoing are not limitations on the scope of the present invention.

Figure 1:
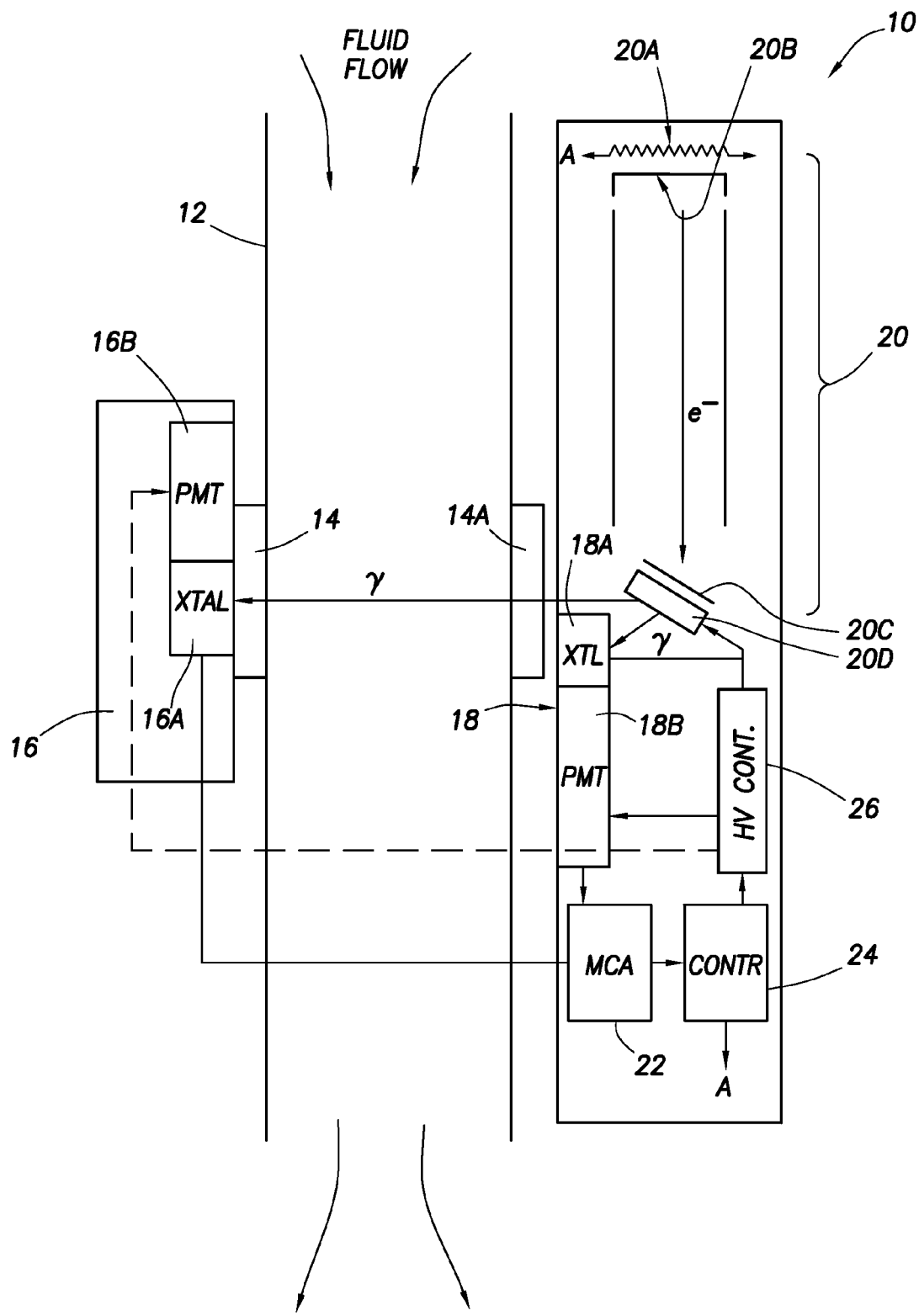
FIG. 1 shows an example fluid analysis device.

An example device for analyzing fluid phase fractional volumes in a multiple phase fluid, particularly wherein the fluid includes a high fractional volume of gas (for example, 90 percent or more) is shown schematically in FIG. 1. The device 10 includes a chamber 12 that may be placed in a fluid flow stream, such as on the wellhead of a borehole drilled through subsurface Earth formations. The chamber 12 may be made such that the fluid disposed therein is at ambient pressure of the fluid flow stream. Other components of the device 10 disposed laterally adjacent to the chamber 12 may be enclosed in various housings (not shown) so as to be maintained at surface atmospheric pressure, as is ordinarily the case for certain types of instruments placed in a fluid flow stream. The chamber 12 is shown in FIG. 1 as being cylindrical, however the particular shape of the chamber 12 is not intended to limit the scope of the invention. For example, a "venturi" type chamber, as shown in U.S. Pat. No. 6,097,786 issued to Groves et al. and assigned to the assignee of the present invention, may be used in some examples. In such examples, it may be possible to calculate a volumetric flow rate of each phase of the fluid sample being analyzed by measuring pressure drop within the venturi and determining the volume fraction of each phase in a manner such as will be explained below. By determining pressure drop and fluid phase volume fraction of each phase, the flow rate of each phase may be determined using techniques known in the art.

Samples of fluid to be analyzed generally pass through the chamber 12 where they are exposed to x-rays ($\gamma$) generated by an x-ray generator 20 forming part of the device 10. X-rays passing through the fluid sample are detected by a measurement detector 16, the output of which is used to characterize the sample of fluid passing through the chamber 12. Operation of the x-ray generator 20 and the measurement detector 16 will be further explained below.

A radiation transparent window 14, 14A may be disposed on laterally opposite sides of the chamber 12 so as to define a radiation path having an inlet into the chamber 12 and an outlet from the chamber 12. The windows 14, 14B may be made from a material, for example boron carbide ($B_4C$), that will transmit photons having selected energy therethrough while attenuating the radiation by at most a selected amount. The material is preferably able to withstand fluid pressure in the flowline as well as being able to transmit radiation as explained above. In the present example, the windows 14, 14A may each be about 4 mm thickness, such that x-ray energy photon radiation having energy in a range of between about 18 to 60 keV (thousand electron volts) will be attenuated by both the windows 14, 14A at most by about 90 percent. Thus, the intensity of the x-ray energy photon radiation applied to the exterior (away from the chamber 12) face of one window (14A in FIG. 1) is reduced by at most about 90 percent by the time it reaches the outer face of the opposite window (14 in FIG. 1) when the chamber 12 is empty. The thickness of the windows 14, 14A may be selected to resist failure to a selected hydrostatic pressure. In the present example the windows 14, 14A may resist external pressure up to 15,000 pounds per square inch.

The measurement detector 16 may be coupled to or otherwise disposed proximate to the exterior face of the opposite window 14 and as explained above is arranged to detect radiation after it passes through any material (not shown in FIG. 1) disposed within the chamber 12. The measurement detector 16 may be a scintillation counter including a scintillation crystal 16A coupled to a photomultiplier 16B. As is known in the art, radiation entering the crystal 16A will cause the crystal to produce flashes of light, the amplitude of which is proportional to the energy of the entering radiation. In some examples, the scintillation crystal 16A may include an energy calibration source ("seed source"—not shown) therein. Such seed source may be used to enable calibration of the output of the measurement detector 16 so that the absolute energy level of entering x-ray and other photons is determinable. See, for example, U.S. Pat. No. 4,879,463 issued to Wraight et al. and assigned to the assignee of the present invention. One non-limiting example of such a calibration source is the isotope Cesium 137, which emits monochromatic gamma rays at an energy level of about 662 keV. In some examples, the measurement detector may include ancillary devices configured to maintain stability of detection with respect to intensity and energy level of incoming radiation. One such detector and ancillary devices is described in International Patent Application Publication No. WO 2001/096902 filed by Perciot et al. Such detector used in the device 10 may provide the advantage of higher accuracy than examples of the device 10 using other types of radiation detector because of the very high stability offered by the disclosed detector.

Radiation to make the measurements for characterizing fluid in the chamber 12 may be provided by the x-ray generator 20. The x-ray generator 20 may include a thermally actuated cathode 20B made from a material that is susceptible to emission of electrons ($e^-$) when heated. The source of heat in the x-ray generator 20 may be a resistance type heater 20A. Electrons emitted by the cathode 20B may be maintained at a high negative voltage relative to a target anode 20C, such that the electrons emitted by the cathode 20B are attracted to and strike the target anode 20C. In such examples, the target anode is at ground potential. A possible advantage of such configuration is elimination of the need to electrically isolate the target from the exterior of the generator, thus simplifying construction and increasing reliability of the generator. In the present example, the target anode 20C (or simply "target") may be made from metallic gold foil, having thickness selected to substantially stop passage therethrough of electrons having energy less than about 100 keV, but enabling relatively free transmission of x-rays having energy above about 10 keV. The target end of the x-ray generator 20 may include suitable shielding (not shown separately) so that x-rays may reach the measurement detector 16 and a reference detector 18 essentially only along direct travel paths as shown in FIG. 1. A filter 20D is disposed proximate the face of the target 20C opposed to the face exposed to electrons from the cathode 20B. The function and structure of the filter 20D will be further explained below. Although not shown in FIG. 1, the foregoing components of the x-ray generator 20 are typically disposed in an evacuated housing. An x-ray output through the wall of such housing (not shown), typically proximate the target 20C and the filter 20D, may be made through a radiation transparent, pressure resistant window (not shown) such as can be made from beryllium. One example of such a window may be a beryllium plate or disk having thickness of about 0.25 mm. Some of the x-rays emanating from the x-ray generator 20 may travel directly to a reference detector 18 disposed proximate the x-ray generator 20. The reference detector 18 may be a scintillation counter, similar in structure to the measurement detector 16, and may include a scintillation crystal 18B and a photomultiplier 18A. In some examples, the reference detector crystal 18B may include a seed source (not shown) as explained above. In other examples, the reference detector 18 may be similar in structure to the detector disclosed in the International Patent Application Publication No. WO 2001/096902 filed by Perciot et al. set forth above.

Output of each photomultiplier 16B, 18B may be coupled to a multichannel pulse height analyzer ("MCA") 22 disposed within or proximate to the other components of the device 10. The MCA 22 may generate a digital bit or count, or similar signal corresponding to each electrical pulse from each photomultiplier 16B, 18B having a selected amplitude, or having amplitude within a selected amplitude range. Thus an output of the MCA 22 may include numbers of counts for each of a selected number of energy "windows" (ranges) detected by each detector 16, 18 within selected time intervals. The counts from the MCA 22 may be coupled to a controller 24, which may be any microprocessor based device, for analysis as will be further explained below.

A high voltage controller 26 may provide actuation voltage for each of the photomultipliers 16B, 18B and the target 20C. In the present example, the cathode 20A, 20B may be maintained at high voltage, and the target 20C maintained at ground potential. The high voltage controller 26 may operate under control of the controller 24 so that a selected voltage is applied to each of the photomultipliers 16B, 18B and the target 20C at all times. The controller 24 may also provide a control signal to the heater 20A to adjust its output so that an electrical current flowing through the generator 20 to the target 20C (called "beam current") is maintained at a selected value for any selected value of high voltage applied to the target 20C. The manner of controlling the beam current and target voltages will be further explained below. In other examples, a separate high voltage controller may be used for the photomultipliers 16B, 18B and the x-ray generator 20.

Figure 1A:
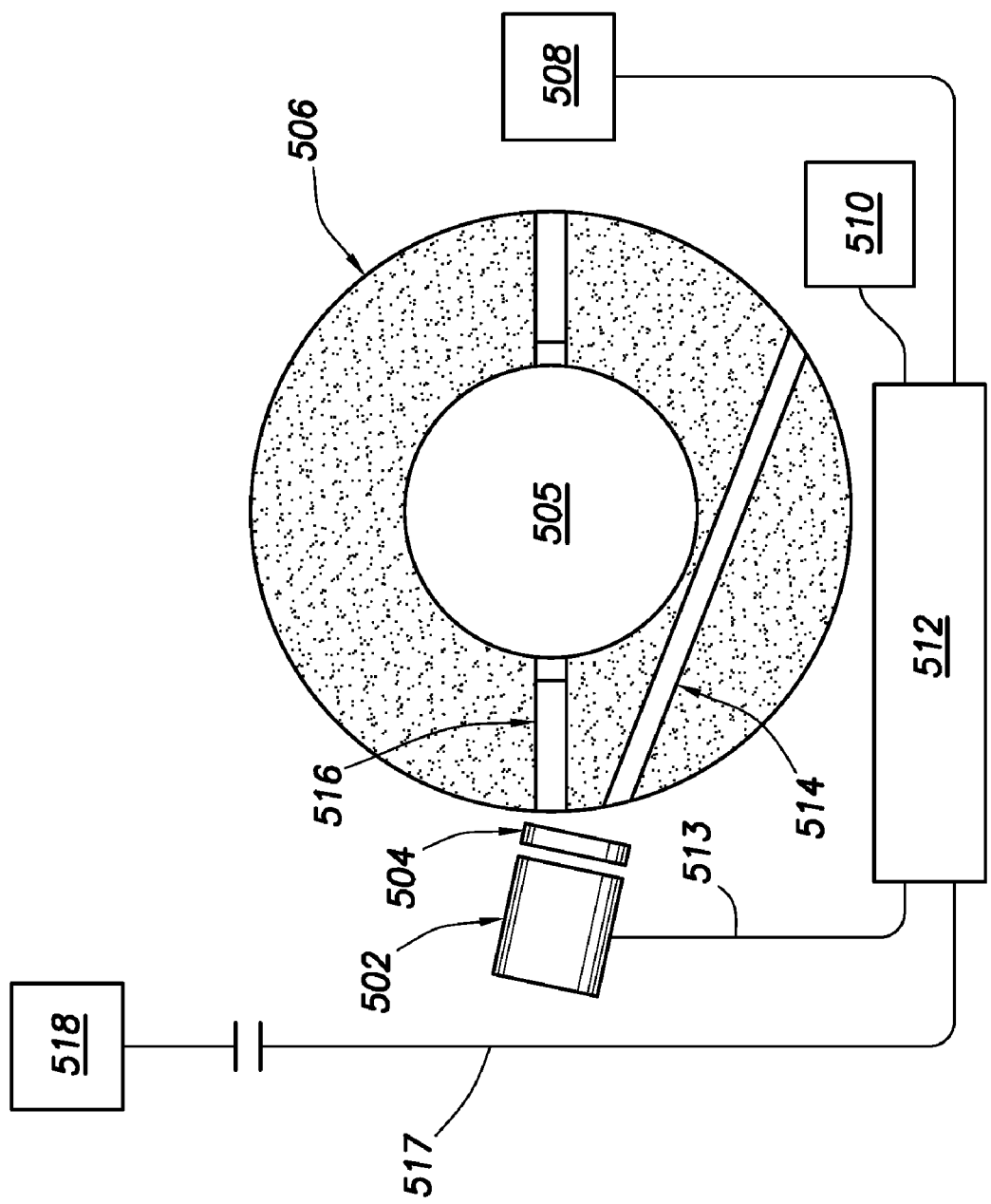
FIG. 1A shows another example fluid analysis device.

Another example is shown in FIG. 1A. Sample fluid flows through a channel 505 in a sample cell 506 which in the present example can be a venturi chamber. In response to input high voltage, an x-ray generator 502 creates radiation that is passed through a filter 504. The filtered radiation can then travel along two paths. Note that for optimal performance, the x-ray generator 502 may be positioned symmetrically with respect to the two paths so that the effect of the filter 504 on the radiation traversing the two paths is as nearly identical as possible. A first path 516 is a measurement path where radiation is passed through the sample cell 506 and fluid in the channel 505 therein and on to the measurement detector 508. The second path 514 is a reference path where radiation is passed directly from the x-ray generator 502 to the reference detector 510. In one example, the outputs of the two radiation detectors 508, 510 are routed to a control and acquisition system 512, which is also connected to the x-ray generator 502 via a cable or wireline 513. Information from the detectors is forwarded from the acquisition system along a cable or wireline 517 to an analysis unit 518.

In examples of a device for determining phase composition of "wet gas" mixtures, that is, mixtures of natural gas including at most about 10 percent brine and/or liquid hydrocarbon, a thickness and composition of the filter 20D, an operating voltage for the x-ray generator 20 (applied between the cathode 20B and the target 20C) and a beam current in the x-ray generator 20 are selected such that a resolution of the device 10 is optimized with respect to changes in composition of the liquid phase components of such a wet gas mixture.

The following conditions are related to the thickness and composition of the filter 20D and the target current and target voltage (cathode). First, in the present example, the target 20C is a 5 micron thick gold foil. Such thickness and composition of foil produce a Brehmsstralung x-ray radiation spectrum that has been determined to be suitable for purposes of the invention. The filter 20D is selected so that the energy spectrum of x-rays entering the chamber 12 through the entry window 14A includes two, distinct energy peaks (local maxima of numbers of photons at each of two distinct energy levels), defined herein as a low energy ("LE") peak and a high energy ("HE") peak. Preferably, the LE peak is as low as practical to enhance sensitivity of the measurements to discriminate between oil and water.

Figure 2:
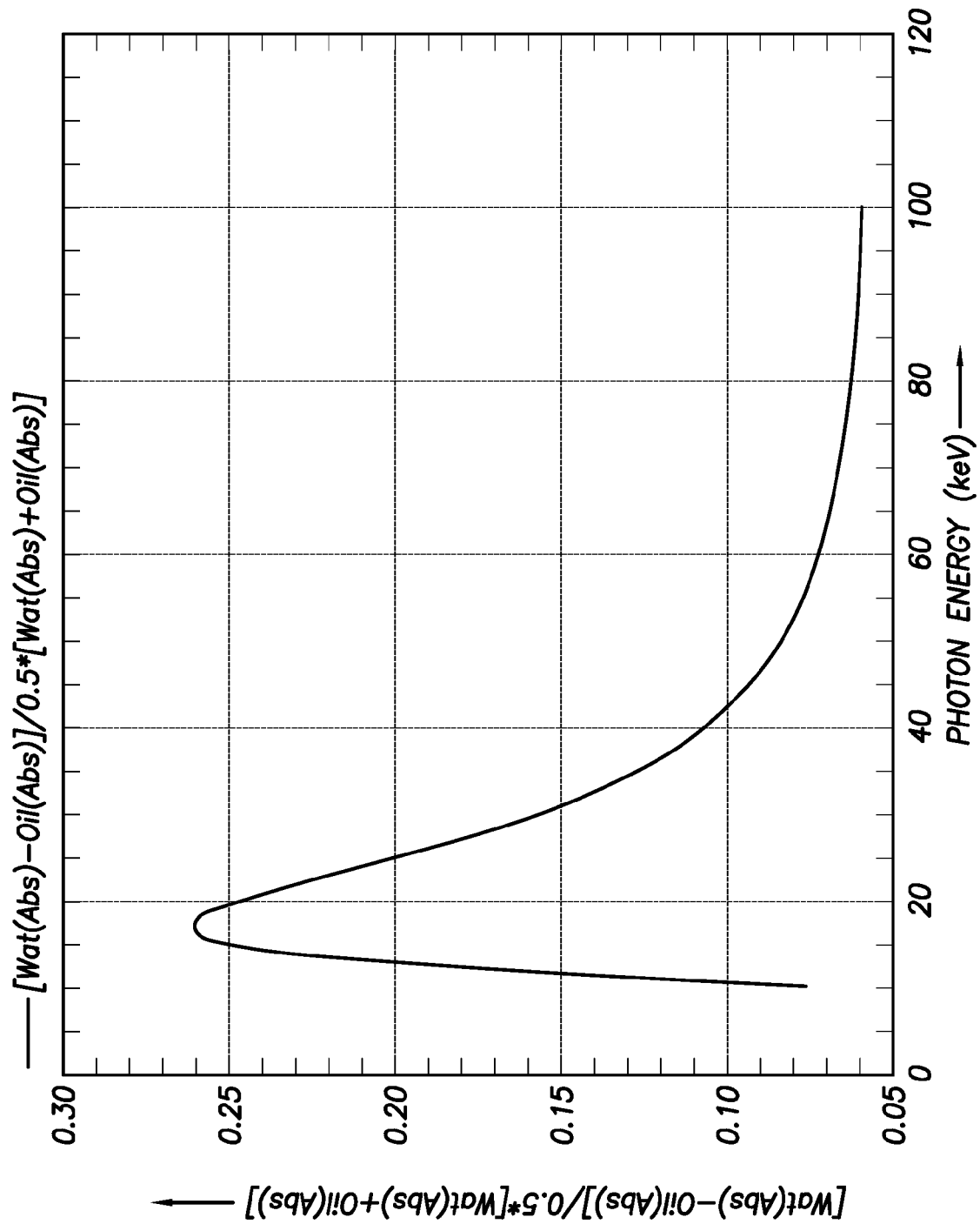
FIG. 2 shows a graph of sensitivity of an instrument to oil and water liquid fractions as a function of energy of radiation used to make measurements.

It has been determined through numerical simulation of response of a device such as the one shown in FIG. 1 that a mixture of 10 percent oil in 90 percent gas, at a pressure of 5,000 pounds per square inch and a temperature of 100 degrees C. will have a maximum x-ray attenuation contrast as compared with a mixture of 10 percent water in 90 percent gas under the same pressure and temperature conditions at an x-ray energy of about 18 keV. A graph showing difference between absorption response with water as the liquid phase and oil as the liquid phase is shown in FIG. 2. One characteristic of the filter 20D therefore, is to have relatively high energy absorption for photons only above about 18-20 keV. Examples of materials having a "K-absorption edge" at a suitable value are shown in Table 1 below. "K-absorption edge" refers to the threshold energy required to energize electrons in the K-shell orbit about the atomic nucleus so that the electrons are ejected from the atom.

TABLE 1

X-ray Absorption Edges

| Element | K Edge |
|---|---|
| Y | 17.0384 |
| Zr | 17.9976 |
| Nb | 18.9856 |
| Mo | 19.9995 |
| Tc | 21.0440 |

Based on the foregoing simulation, it has been determined that a suitable material for the filter 20D can be an element having atomic number (Z) in a range of about 38 to 45 or mixtures of such elements. In the example, the filter 20D can be made from molybdenum. Molybdenum (Mo) has a characteristic x-ray absorption "edge" at 19.9995 keV. By using such a filter, energy above the absorption edge is substantially attenuated from the Brehmsstralung x-ray energy spectrum above the absorption edge until the x-ray energy is closer to the Brehmsstralung endpoint energy.

Figure 3:
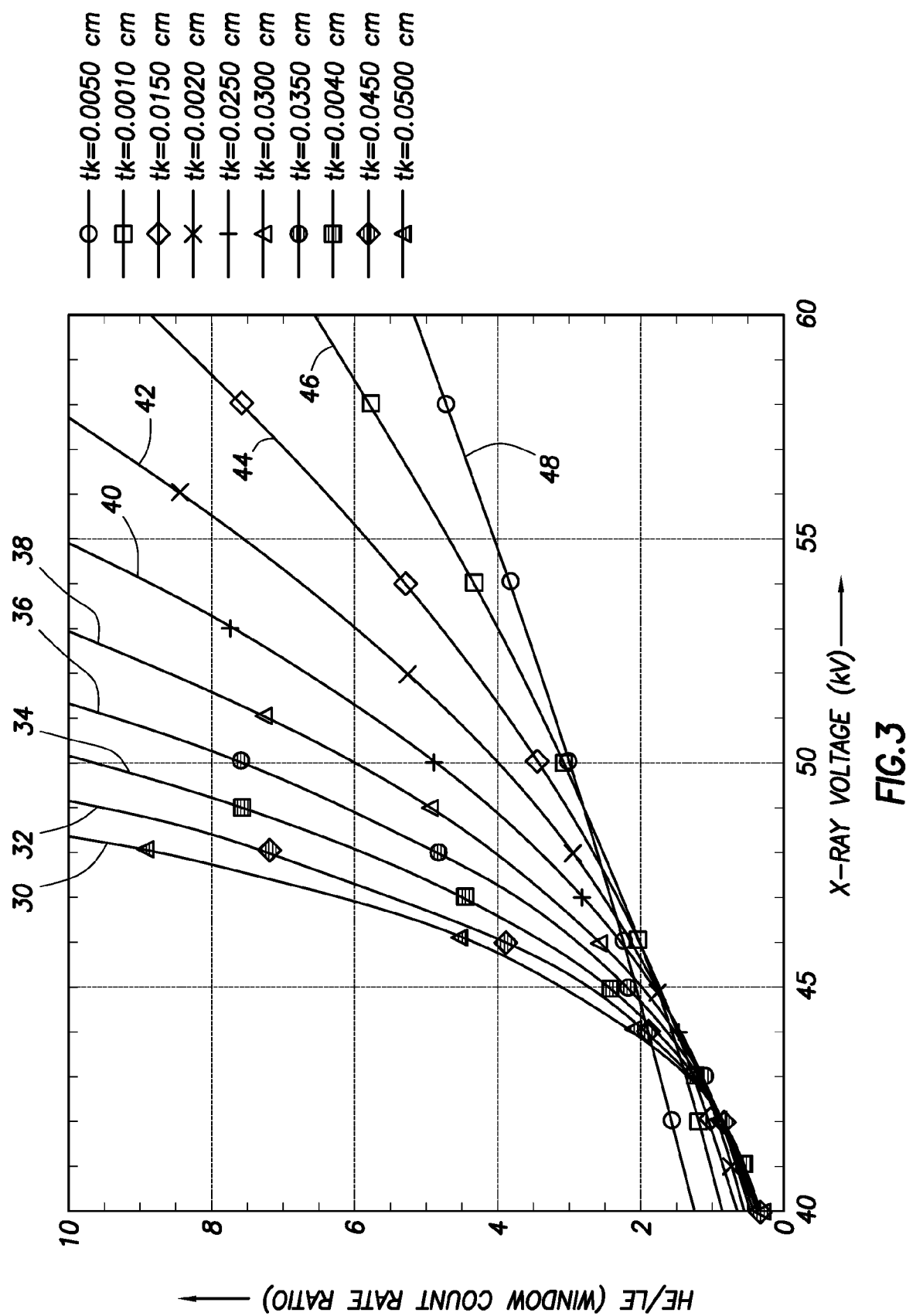
FIG. 3 shows a graph of detector counting rate ratios for various thicknesses of radiation filter for various x-ray target voltages.

Having selected a suitable filter material, the thickness thereof and operating voltage that may be used in some examples was determined by simulation of a device such as shown in FIG. 1. FIG. 3 shows a graph of simulated counting rate ratios (ratios of counts detected in the HE window with respect to counts detected in the LE window) for various filter thicknesses and x-ray generator target voltages at curves 30 through 48. Filter thickness ranges from 50 microns (curve 30) to 500 microns (curve 48). A ratio of count rates of x-rays having energy around the HE peak and around the LE peak may be in the range from about 10 to 1. It has been determined from such numerical simulation that a practical range for target voltage is about 40 to 50 kV.

Figure 4:
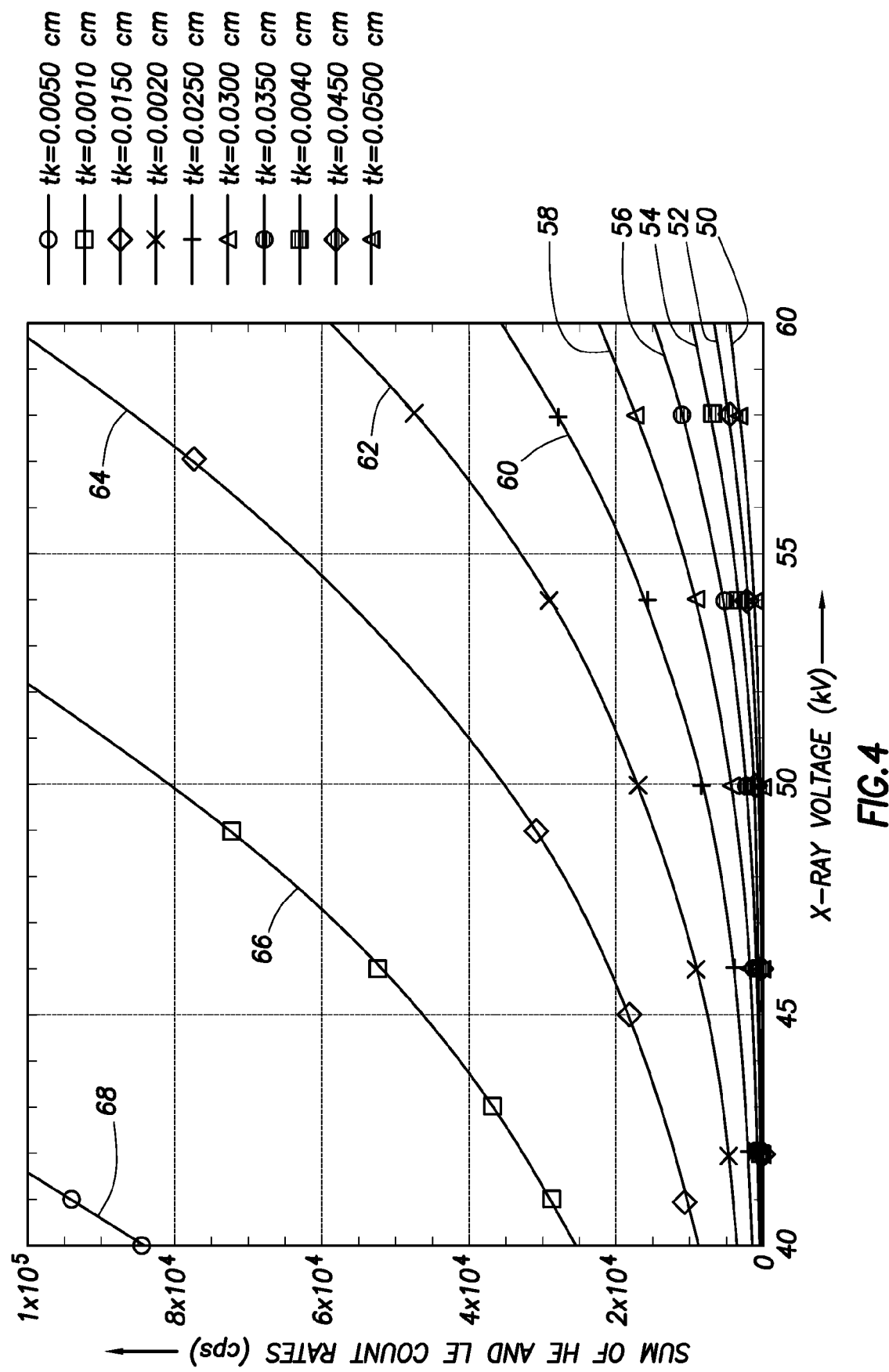
FIG. 4 shows a graph of detector counting rates for various thicknesses of radiation filter for various x-ray target voltages.

It is believed that a total count rate (HE plus LE) should be at least $1 \times 10^4$ counts per second per microampere of electron beam current. For an x-ray generator operating voltage in the range of about 40 to 50 kV, the maximum filter thickness is believed to be about 0.25 mm (250 microns). A graph of total counting rate with respect to various target voltages and various Mo filter thicknesses is shown by curves 50 through 68 in FIG. 4. Based on the foregoing analysis, a target voltage in some examples may be about 47 kV for a Mo filter thickness of about 250 microns.

Figure 5:
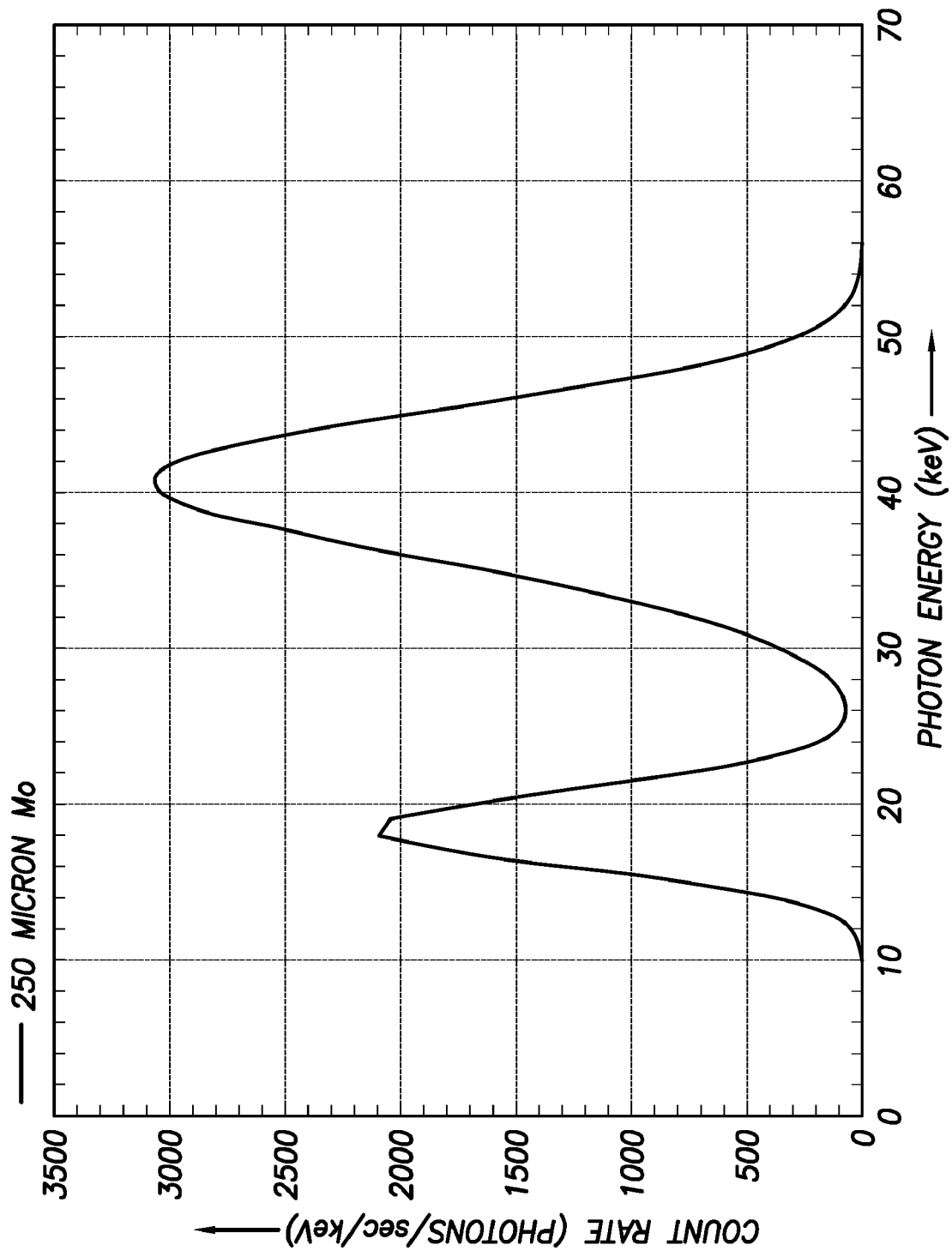
FIG. 5 shows an example x-ray energy spectrum produced by filtering x-rays and operating an x-ray generator at a selected target voltage.

FIG. 5 shows a graph of a photon energy spectrum with detector resolution broadening for an x-ray generator operating at 47 kV, with an empty chamber having 4 mm thick $B_4C$ windows (see 14 and 14A in FIG. 1, representing a total $B_4C$ thickness of 8 mm) and a 0.0250 cm thick filter made from molybdenum.

The mean energies of the LE and HE peaks are 18.6 and 41.5 keV respectively. Thus, two well defined energy peaks with a small radiation flux at intermediate energies can be created from a Brehmsstralung x-ray spectrum by suitable selection of filter material, filter thickness and x-ray generator operating voltage.

Referring again to FIG. 1, in the present example, the controller 24 may be programmed to count numbers of photons detected by the reference detector 18 in a HE "window" and a LE "window" during selected time intervals. The HE window and the LE window may be a predetermined range of contiguous MCA channels (each such range generally centered around the HE peak and the LE peak, respectively, for the HE and LE windows) or other selected channels of the channel range of the MCA 22. In some examples, the LE window may be configured such that counts corresponding to x-ray energy between about 10 to 30 keV will cumulate to the LE window. The HE window may be configured such that counts corresponding to x-ray energy between about 30 to 55 keV cumulate to the HE window.

For each such time interval, or for selected time intervals, a ratio of HE window counts to LE window counts may be calculated in the controller 24 for the output of the reference detector 18. Any change in the calculated ratio may be used to adjust the output of the high voltage controller 26 to the x-ray generator 20. It has been determined that the change in calculated HE to LE count rate ratio is linearly related to the voltage applied to the x-ray generator 20 for small variations from the nominal operating voltage. In one example, the change in calculated ratio is used to adjust the voltage to maintain a substantially constant ratio of HE window counts to LE window counts measured by the reference detector 18. In addition, the change in the sum of the HE and LE count rate can be used to adjust the x-ray tube electron beam current to maintain substantially constant sum of HE and LE window counts measured by the reference detector 18.

To compensate for any changes in total x-ray photon output of the x-ray generator 20, in making measurements using the device shown in FIG. 1, counts measured in each of a selected number of time intervals for each of the HE window and the LE window by the measurement detector 16 are normalized by the counts in each of the HE and LE windows from the reference detector 18 during the same time intervals.

In order to determine the phase fractions of oil, gas, and water in a sample of fluid, counts from the measurement detector 16 from the HE window and the LE window in selected time intervals are processed as follows. The HE window count measurements correspond to the following equation:

$$I_{M_H} = I_{M_H}^{(0)} e^{-[\mu_o(H)d\alpha_o + \mu_w(H)d\alpha_w + \mu_g(H)d\alpha_g]}$$

where $I_{M_H}$ represents the number of HE counts detected by the measurement detector 16, $I_{M_H}^{(0)}$ represents the number of HE counts when the radiation is passed through the chamber 12 when it is empty, d represents the diameter (photon path length) of the sample cell, $\alpha_o$ represents the fluid phase fraction of oil, $\alpha_w$ represent the fluid phase fraction of water, and $\alpha_g$ represent the fluid phase fraction of gas. $\mu_o(H)$, $\mu_w(H)$ and $\mu_g(H)$ represent the linear attenuation of the oil, water and gas phases respectively for the HE window. These values are dependent upon the energy of the X-rays, the composition and density of the oil, water and gas phases. These fractions are the subject of interest. The LE window count measurements correspond to the following equation:

$$I_{M_L} = I_{M_L}^{(0)} e^{-[\mu_o(L)d\alpha_o + \mu_w(L)d\alpha_w + \mu_g(L)d\alpha_g]}$$

where $I_{M_L}$ represents the number of LE counts detected by the measurement detector 16 and $I_{M_L}^{(0)}$ represent the number of low energy counts when the radiation is passed through the empty sample chamber 12. $\mu_o(L)$, $\mu_w(L)$ and $\mu_g(L)$ are different coefficients for the LE window. Both of the foregoing equations can be rearranged to provide the following:

$$-\ln\left(\frac{I_{M_H}}{I_{M_H}^{(0)}}\right) = \mu_o(H)d\alpha_o + \mu_w(H)d\alpha_w + \mu_g(H)d\alpha_g$$

for the HE window measurements:

$$-\ln\left(\frac{I_{M_L}}{I_{M_L}^{(0)}}\right) = \mu_o(L)d\alpha_o + \mu_w(L)d\alpha_w + \mu_g(L)d\alpha_g$$

for the LE window measurements. A further equation is needed to solve for the three fluid fractions. The sample fluids comprise oil, water, and gas, so it is also known that:

$$\alpha_o + \alpha_w + \alpha_g = 1$$

Using these three foregoing equations, the fluid fractions of oil, water, and gas can be determined based on the radiation passed through the sample that is detected in each of the LE window and HE window by the measurement detector. In analyzing fractional volumes of the above three constituent phases, certain assumptions are made with respect to density and composition of each phase. Density is readily determinable when temperature and pressure of the gas are known. Sensors (not shown in the figures) may be used in association with the device 10 to determine pressure and temperature for determining gas density.

It will be appreciated by those skilled in the art that the above analysis relies solely on counts from the measurement detector 16 to determine the volume fractions of various phases in a fluid sample. It is possible, given a sufficiently stable type of measurement detector and x-ray generator, to use only the measurement detector for such volume fraction determination. Practical examples of a device, however, may benefit from the use of a reference detector as explained herein.

A fluid phase fraction analysis device according to the various aspects of the invention may provide improved accuracy when used in fluids having high fractional volume of gas (e.g., 90 percent or more) than devices known in the art.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An apparatus for determining fractional amounts of each phase of a multiple phase fluid, comprising:
    an x-ray generator configured to output x-rays by accelerating electrons into a target material;
    a sample chamber configured to admit therein a sample of fluid for analysis and disposed in a radiation path of an output from the x-ray generator;
    a filter disposed in the radiation path between the output of the x-ray generator and a radiation input of the sample chamber;
    a first radiation detector positioned in the radiation path from the sample chamber after radiation has passed through the sample chamber, the first radiation detector being configured to detect x-rays in selected energy ranges that have passed through the sample chamber; and
    a means for determining fractional volumes of gas, oil and water from the detected x-rays; and
    wherein a maximum thickness of the filter is about 250 microns and a material of the filter comprises molybdenum so as to optimize resolution of radiation detected by the first radiation detector to changes in volume fraction of oil and water in the fluid sample when a gas volume fraction thereof is between about 90 to 100 percent.

2. The apparatus of claim 1 further comprising an electrical power source operable to cause the generator to emit x-rays, a voltage of the power source selectable to maintain a selected counting rate in each of a plurality of energy ranges by a second radiation detector.

3. The apparatus of claim 1 further comprising a pulse height analyzer operably coupled to an output of the first radiation detector.

4. The apparatus of claim 3 further comprising a second radiation detector disposed in the radiation output path of the generator, the pulse height analyzer coupled to an output of the second radiation detector and configured to generate counts corresponding to x-rays detected by the second radiation detector in selected energy ranges, and a controller operably coupled to the pulse height analyzer, the controller configured to adjust at least one of voltage and a beam current of the x-ray generator in response to radiation detected in the selected energy ranges by the second radiation detector.

5. The apparatus of claim 1 wherein the filter comprises at least one of an element with an atomic number in the range Z=38 to 45 and mixtures of such elements.

6. The apparatus of claim 1 wherein the sample chamber comprises an x-ray transparent window in the radiation path in each of a radiation input and a radiation output thereof, each of the windows made from a material having composition and thickness selected to attenuate radiation by at most a selected amount and to resist hydrostatic pressure to a selected amount.

7. The apparatus of claim 6 wherein the windows comprise boron carbide.

8. The apparatus of claim 1 wherein the x-ray generator operating voltage is in the range of about 40 to 50 kV.

9. A method for determining volume fraction of selected components of a fluid, comprising:
    generating x-rays by accelerating electrons into a target material;
    controlling at least one of acceleration and current of electrons and filtering the generated x-rays such that the filtered x-rays have a predetermined energy spectrum optimized to resolve volume fractions of oil and water disposed in gas, wherein a volume fraction of the gas is between about 90 and 100 percent;
    passing the filtered x-rays through a sample of the fluid;
    detecting x-rays in selected energy ranges that have passed through the fluid sample; and
    determining fractional volumes of gas, oil and water from the detected x-rays,
    wherein the filtering includes using a filter with a maximum thickness of about 250 microns and a material of the filter comprises molybdenum.

10. The method of claim 9 further comprising directly detecting filtered x-rays in the selected energy ranges, and normalizing the numbers of detected x-rays having passed through the sample of fluid with respect to numbers of directly detected filtered x-rays.

11. The method of claim 9 further comprising directly detecting filtered x-rays in the selected energy ranges, and controlling accelerating the electrons based on number of x-rays directly detected in each of the selected energy ranges.

12. The method of claim 9 further comprising accelerating the sample of fluid, measuring a pressure drop in the sample of fluid resulting from the acceleration, and calculating a flow rate of the gas, oil and water from the measured pressure drop and the determined volume fractions.

13. The method of claim 9 wherein the determining fractional volumes comprises determining numbers of detected x-rays in each of a plurality of energy ranges.

14. The method of claim 9 further comprising operating the x-ray generator with a voltage in the range of about 40 to 50 kV.

* * * * *